United States Patent [19]

Rothman

[11] 4,421,111
[45] Dec. 20, 1983

[54] LOW-VOLTAGE SURGICAL CAST CUTTER WITH VACUUM EXHAUST OF DEBRIS

[75] Inventor: Neil S. Rothman, Baltimore, Md.

[73] Assignee: Black & Decker Inc., Newark, Del.

[21] Appl. No.: 353,917

[22] Filed: Mar. 2, 1982

[51] Int. Cl.³ .............................................. A61F 5/04
[52] U.S. Cl. .................................... 128/91 A; 30/124
[58] Field of Search ................... 128/91 A, 91 R, 83; 30/123, 124, 167; 51/273; 15/327 R, 327A–327 F

[56] References Cited

U.S. PATENT DOCUMENTS

| | | | |
|---|---|---|---|
| 2,232,733 | 2/1941 | Scarboro | 30/167 |
| 2,929,177 | 3/1960 | Sheps | 51/273 |
| 2,958,894 | 11/1960 | Carabet | 15/327 |
| 3,103,069 | 9/1963 | Gary | 30/124 |
| 3,481,036 | 12/1969 | Slaughter | 30/124 |
| 3,973,179 | 8/1976 | Weber et al. | 320/2 |
| 4,309,067 | 1/1982 | Riley, Jr. | 339/91 R |

*Primary Examiner*—John D. Yasko
*Attorney, Agent, or Firm*—R. B. Sherer; H. Weinstein; Charles E. Yocum

[57] ABSTRACT

A surgical cast cutter or other power tool comprises a main tool section and a complementary hose section releasably secured to the tool section rearwardly thereof. The sections have respective cooperating rib means formed therein which slidably engage each other (in a direction transverse to the longitudinal axis of the tool section) as the sections are brought together; and the sections are retained by a releasable latching means. A low-voltage electric motor in the tool section drives a transmission which oscillates a cutter mounted forwardly of the tool section. A debris conduit in the tool section communicates with an opening formed in the hose section when the sections are joined together. The hose section carries a flexible vacuum hose communicating with the opening therein, thereby facilitating removal of dust particles generated during operation of the cutter to remove a plaster cast. A low-voltage cable is carried by the vacuum hose and is connected to electrical contacts carried by the hose section. These contacts engage corresponding electrical contacts carried by the tool section, when the sections are brought together, for energization of the motor through a switch carried by one of the sections. The sections have respective side housing edges which are inclined with respect to the respective cooperating rib means; these side housing edges are brought into substantial abutting engagement when the sections are fully joined. The opening in the hose section, as well as the rearward opening of the debris conduit, are also inclined with respect to the respective cooperating rib means to assure good sealing engagement therebetween when the sections are fully joined.

9 Claims, 8 Drawing Figures

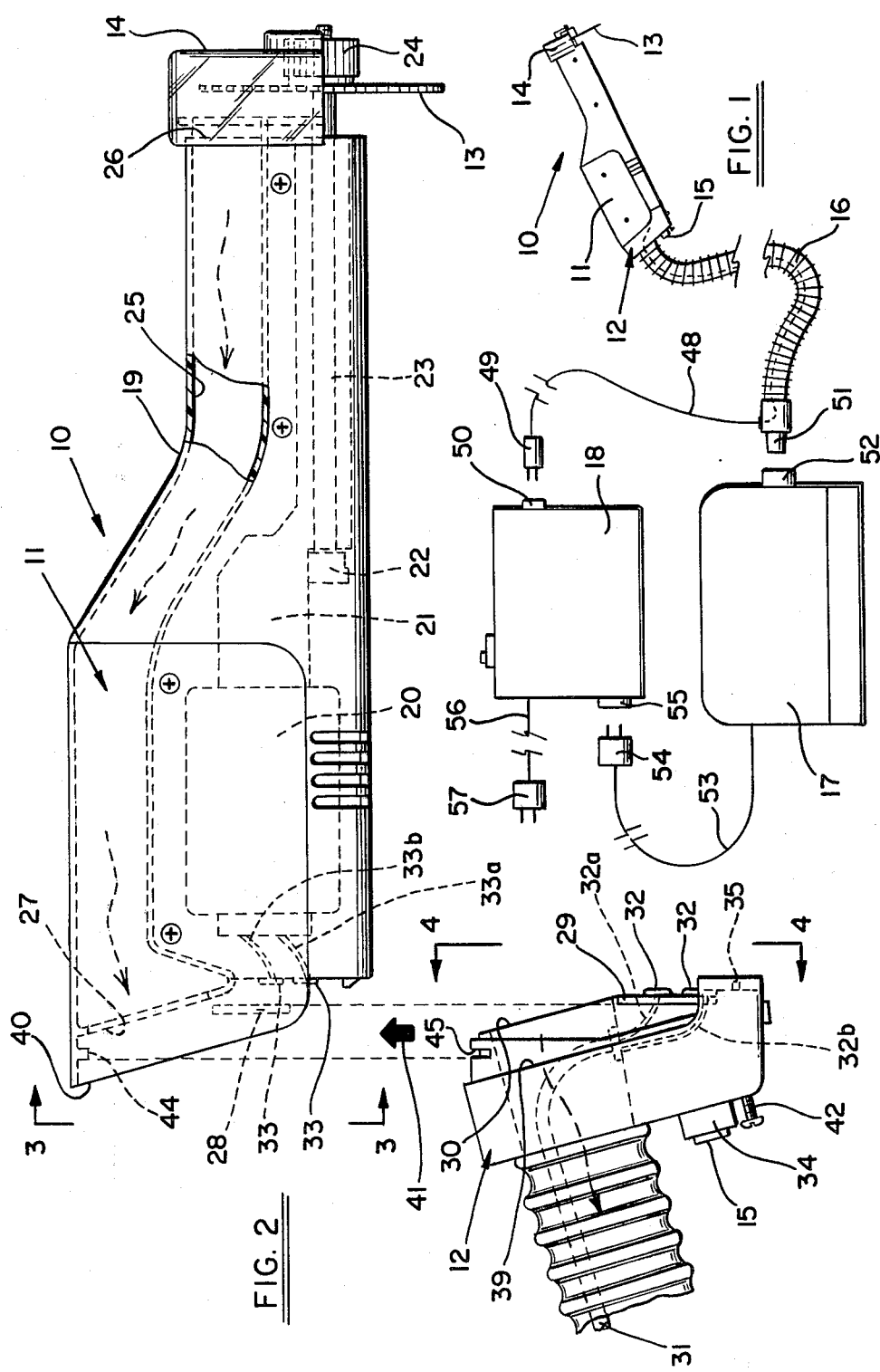

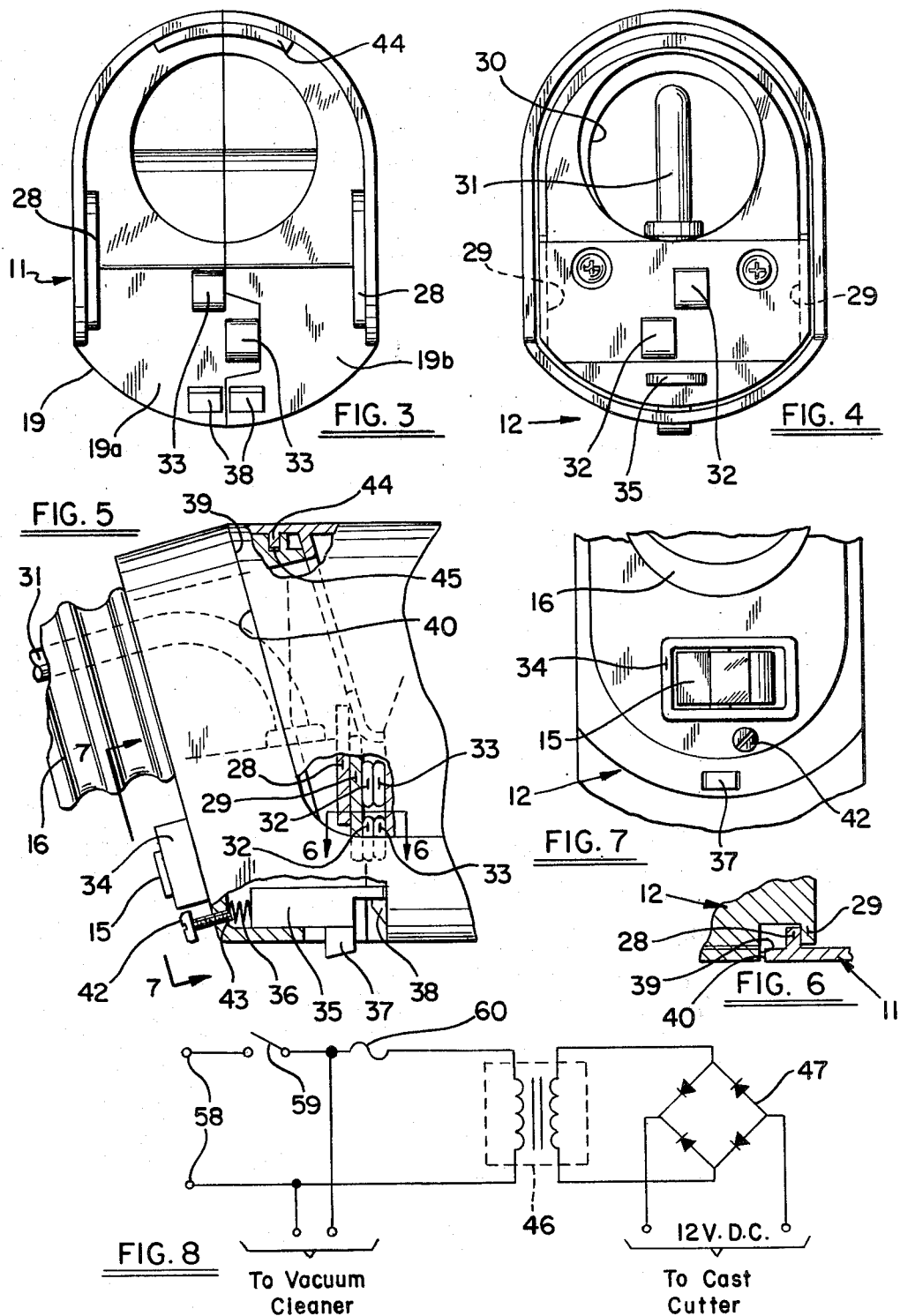

LOW-VOLTAGE SURGICAL CAST CUTTER WITH VACUUM EXHAUST OF DEBRIS

BACKGROUND OF THE INVENTION

Surgical cast cutters have been employed for many years. These tools are portable and have a small circular saw blade or cutter that oscillates through a limited angle, thereby assuring that the patient will not be injured while the cast is being removed. The oscillating cutter is driven by a suitable transmission, which may include a bifurcated fork, and the transmission is driven by an electric motor housed in the tool. The motor is usually an a.c. motor supplied by line voltage.

Because of the dust and debris generated by the cutter during removable of the plaster cast, the prior art (as exemplified by U.S. Pat. Nos. 3,103,069 and 3,481,036) has resorted to a built-in impeller or fan for generating a vacuum exhaust. The fan is driven directly by the rear end of the motor shaft and communicates with one end of a debris conduit or channel suitably formed in the housing to one side of the motor. The other end of the conduit terminates forwardly of the tool housing and adjacent to the cutter. As a result, the dust and debris are withdrawn from the vicinity of the cutter and are deposited laterally of the fan in a receptable carried by the tool.

Another prior art teaching of a surgical cast remover with a vacuum exhaust of the dust particles is U.S. Pat. No. 2,232,733, wherein the cutter is driven by a flexible power shaft, and wherein the vacuum hose is disposed substantially parallel to the flexible power shaft and terminates in a dust bag remote from the cutter. Moreover, in the general art relating to portable electric tools and appliances, it is well known to attach a vacuum hose to the housing of the tool for removal of the dust, debris or other particles generated during operation of the tool, and to connect the hose to a conventional vacuum cleaner located remotely from the tool; such an arrangement is exemplified by U.S. Pat. No. 2,929,177.

While these prior art designs and structural arrangements of surgical cast cutters and the like may be somewhat adequate for the purposes intended, nevertheless, there are a number of inherent disadvantages or deficiencies associated therewith, the more significant of which may be enumerated as follows: (1) the overall tool is relatively heavy and bulky, hence somewhat cumbersome, awkward and inconvenient to use; (2) the motor is operated from line voltage, which requires suitable insulation to maintain electrical safety requirements; (3) the a.c. motor is fairly large and runs at a relatively high speed, thereby increasing the ambient vibration levels, and as a result, any prolonged usage of the tool may become somewhat uncomfortable and tiring; (4) the motor-driven exhaust fan generates relatively high noise levels, which can become irritating in the usually serene atmosphere of a clinic or hospital. (5) the cost of original manufacture and assembly, as well as the cost of subsequent service and repair, are relatively expensive; and (6) the designs concentrate on a single-purpose tool, hence are relatively inflexible, and are not really adaptable to a broad line of related products for medical and other purposes.

SUMMARY OF THE INVENTION

Accordingly, it is an object of the present invention to alleviate the deficiencies of the prior art by providing a substantially improved surgical cast cutter.

It is another object of the present invention to provide a surgical cast cutter which comprises a main tool section and a complementary hose section removably secured rearwardly thereof, the hose section carrying a flexible hose extending rearwardly thereof and leading to a conventional vacuum cleaner remote from the portable cast cutter.

It is yet another object of the present invention to provide a surgical cast cutter having a housing with a low-voltage electric motor therein, the motor being energized by a low-voltage cable carried by the flexible vacuum hose; and wherein electrical contacts carried by the hose section (and connected to the cable) engage corresponding electrical contacts carried by the tool section, when the sections are brought together.

It is again yet another object of the present invention to provide respective rib means, one on the tool section and the other on the hose section, the rib means being complementary to each other and being formed substantially at right angles with respect to the longitudinal axis of the tool; and wherein the respective side housing edges of the sections are inclined at an acute angle with respect to the complementary rib means, whereby, when the mating sections are brought together in a direction substantially at right angles to the longitudinal axis of the tool, the complementary rib means slidably engage each other to guide the respective inclined side housing edges into substantial abutting engagement, when the sections are fully joined together.

It is a further object of the present invention to provide a rearward opening on the tool section that communicates with a forward opening on the hose section, when the sections are fully joined together, for egress of the dust particles through the rearwardly-extending vacuum hose; and wherein the respective openings are inclined with respect to the complementary guiding rib means on the respective sections, whereby, when the sections are brought together in a direction parallel to the plane of the complementary rib means, the openings become alined with respect to each other with limited wear on the adjacent surfaces and with substantially no air leakage therebetween.

It is a still further object of the present invention to provide a surgical cast cutter which is relatively lightweight, convenient and easy to use, and has relatively low vibration and noise loads associated therewith.

It is a yet still further object of the present invention to provide a surgical cast cutter which has an inherently low-voltage operation, thereby obviating the necessity for rigid electrical insulation requirements.

It is again a yet still further object of the present invention to provide a surgical cast cutter which is more economical to produce and to service, yet has design flexibility for facilitating the marketing of a board line of related products for medical and other uses.

These and other objects of the present invention will become apparent from a reading of the following specification, taken in conjunction with the enclosed drawings.

BRIEF DESCRIPTION OF THE DRAWINGS

FIG. 1 is a side elevation of the improved surgical cast cutter of the present invention, with its remote power supply and vacuum cleaner being shown somewhat schematically, FIG. 2 is an exploded elevation of the mating sections of the surgical cast cutter, drawn to an enlarged scale, and with certain parts broken away and sectioned;

FIG. 3 is a rear elevation of the main tool section, taken along the lines 3—3 of FIG. 2, and drawn to an enlarged scale;

FIG. 4 is a front elevation of the mating hose section, taken along the lines 4—4 of FIG. 3, and drawn to an enlarged scale;

FIG. 5 is a side elevation of respective portions of the mating sections in their fully engaged position, and with parts broken away and sectioned;

FIG. 6 is a detail section view, taken along the lines 6—6 of FIG. 5, and showing the cooperating rib means which slidably engage each other for progressively bringing the mating sections together;

FIG. 7 is a view taken along the lines 7—7 of FIG. 5, showing the switch for energizing the motor, and further showing the screw for selectively disabling the releasable latch and precluding an inadvertent operation thereof; and FIG. 8 is a schematic wiring diagram, showing the high-voltage connection to the vacuum cleaner, and further showing the low-voltage (12 volt) supply to the cast cutter.

DESCRIPTION OF THE PREFERRED EMBODIMENT

With reference to FIG. 1, there is illustrated a surgical cast cutter 10 with which the teachings of the present invention may find more particular utility. However, it will be appreciated by those skilled in the art that the teachings of the present invention are equally applicable to other power tools intended for medical or other purposes, especially wherein similar environmental characteristics or problems are encountered. With this in mind, the surgical cast cutter 10 generally comprises a main tool section 11 formed along a generally longitudinal axis, a generally axially-disposed mating hose section 12 releasably secured to the tool section rearwardly thereof, an oscillating blade or cutter 13 mounted forwardly of the tool section, a combination guard and hood 14 for the cutter, a switch 15 for energizing the unit, a flexible vacuum hose 16 carried by the hose section and extending rearwardly therefrom, a remote vacuum cleaner 17 on the other end of the hose, and a power supply 18.

With reference to FIG. 2, the tool section 11 has a housing 19 with a low voltage (12 volt) motor 20 therein. The motor drives a transmission 21, including a bifurcated fork 22, which is connected to a longitudinal shaft 23 mounted in the housing for limited oscillation therein. It will be appreciated that the transmission, bifurcated fork, oscillating shaft and cutter are all conventional, form no part of the present invention, and hence have been shown somewhat schematically herein; conversely, the scope of the present invention is not to be limited thereby. With this in mind, the cutter (which preferably is circular in plan outline) is mounted on the end of the shaft and is retained thereon by an internally threaded knob 24, the outer surface of which preferably has longitudinally serrations or knurls for facilitating a convenient manipulation. A debris conduit 25 is formed within the housing, preferably above the motor and isolated therefrom. The debris conduit commences in an opening 26 forwardly of the tool; this opening is within the hood and in the vicinity of the oscillating cutter for removal of the dust particles and other debris therefrom. The other end of the conduit terminates in an opening 27 formed rearwardly of the housing for the tool section.

With reference again to FIG. 2, and with further reference to FIGS. 3 through 6, the housing for the tool section comprises a pair of complementary mating halves 19a and 19b joined together along a common longitudinal midplane (as shown more clearly in FIG. 3). These mating halves of the housing are preferably injection molded from a suitable plastic material having good structural rigidity and relatively high impact strength. The rear portion of the tool section housing 19 is formed with rib means which preferably comprises a pair of spaced parallel ribs 28 integrally formed on the respective housing halves in a direction which is transverse to (and preferably, substantially at right angles to) the generally longitudinal axis of the tool section). As shown more clearly in FIG. 4, the complementary hose section 12 has corresponding ribs means which preferably comprises a pair of spaced parallel ribs 29 integrally formed thereon.

When the respective tool sections 11 and 12 are brought together, as shown in FIGS. 5 and 6, the corresponding respective rib means slidably mesh or engage each other (progressively relative to one another) to assure that the respective tool sections will be brought together in a direction which is transverse to (and substantially at right angles to) the generally longitudinal axis or arrangement of the overall tool.

When the sections are brought together, the debris opening 27 in the tool section communicates with an opening 30 formed in the hose section. As shown in FIG. 2, these debris openings 27 and 30 are each inclined at an acute angle with respect to the corresponding rib means in the tool section and hose section, respectively. Thus, as the respective sections are brought together, their respective openings 27 and 30 are brought progressively into a complete alinement with substantially no air leakage therebetween at the adjacent mating surfaces of the respective sections. Otherwise, if the openings were not so inclined, but were formed perpendicular to the longitudinal axis of the tool and parallel to the direction of mating engagement of the respective sections, wear and possibly some deformation may occur on the adjacent surfaces resulting in substantial air leakage between the alined openings. As a consequence thereof, the efficiency of the vacuum dust exhaust would become diminished, and the electrical components of the tool (hereinafter described) would possibly deteriorate because of dust accumulation and resultant contamination.

The surgical cast cutter is energized by a low-voltage cable 31 carried within the flexible vacuum hose (or otherwise formed therein). The use of a low-voltage cable means, aside from surgical cast cutters or the like, is generally known in the art (as exemplified by U.S. Pat. No. 2,958,894). The cable is connected through the switch 15 and suitable conductors to a pair of spaced electrical contacts 32. The conductors, being conventional, have been shown somewhat schematically (as at 32a and 32b) for ease of illustration. The respective contacts 32 project forwardly of the hose section 12 (as shown in FIGS. 2 and 4) and, when the sections are brought together, engage a corresponding pair of electrical contacts 33 carried by the tool section 11 and projecting rearwardly therefrom. The contacts 33 on the tool section are connected to the low-voltage motor by suitable conductors; these conductors are also conventional and hence have been shown somewhat schematically (as at 33a and 33b) for ease of illustration. The switch is preferably of the toggle type and is recessed within a rectangular projecting boss 34 molded integrally with the hose section (as shown in FIGS. 2 and 7).

When the switch 15 is moved into its "on" position to energize the motor, the cutter 13 is oscillated through a small acute angle (of approximately seven (7) degrees in a preferred embodiment) through the conventional driving transmission means. As shown by the small arrows in FIG. 2, the dust particles and other debris generated by the cutter during operation of the tool (to remove a plaster cast or the like) are drawn through the hood 14, forward opening 26 in the tool section 11, debris conduit 25, rearward opening 27, alined opening 30 in the hose section 12, and the flexible hose 16 to the vacuum cleaner 17.

Because of the combination of the low-voltage operation of the motor, together with the vacuum exhaust of the dust particles through a flexible hose projecting rearwardly of the tool and connected to a remote vacuum cleaner, the deficiencies of the prior art are substantially alleviated if not avoided altogether, and the advantage and benefits of the present invention are thus obtained. In partial summary, these advantages are as follows: lightweight, improved portability for convenient usage, efficient removal of the dust particles and other debris, and reduced vibration and ambient noise levels, all in a design that may be manufactured and serviced more economically.

Releasable latching means are provided for maintaining the respective mating sections in their fully joined position. With reference again to FIG. 5, this releasable latching means comprises a latch 35 carried by the hose section, projecting forwardly therefrom, and biased forwardly by a spring 36. The latch may be manually retracted within the hose section (against the resilient bias force of the spring) by means of a release button 37 formed integrally with the latch and projecting through an opening below the hose section, thereby facilitating removal of the hose section from the tool section. Conversely, when the respective sections are brought together (by means of the cooperating respective rib means as previously described) the latch engages a cam ledge 38 molded integrally with the tool section 11 and projecting rearwardly therefrom. The latch rides up over the stationary ledge and "snaps" into place to securely retain the mating sections together. Furthermore, the sections have respective adjacent side housing edges 39 and 40 (as shown in FIGS. 2 and 5) which are inclined at an acute angle with respect to the cooperating respective rib means. This assures that as the sections are brought together, in the direction of the arrow 41 (in FIG. 2) and substantially at right angles to the generally longitudinal axis of the tool, that the respective inclined side housing edges 39 and 40 will not interfere with the desired sliding action between the sections and will eventually be brought into substantial abutting engagement therebetween.

Aside from a surgical cast cutter or the like, the relative movement between a pair of mating housing sections (in a direction substantially perpendicular to the generally longitudinal axis of the tool) together with the cooperating rib means, inclined respective housing edges, mating electrical contacts carried respectively by the sections, and releasable latching means—are all generally known in the power tool field (as evidenced by U.S. Pat. No. 3,973,179). However, it is the application of those concepts and structures to a surgical cast cutter or the like, and especially to a surgical cast cutter having a low-voltage operation and a vacuum hose projecting rearwardly therefrom for efficient collection of the dust particles by a remote vacuum cleaner, which is new and constitutes a substantial contribution to this specific and well-developed art.

Moreover, the surgical cast cutter of the present invention provides additional structure, unique to its environment, which has not been disclosed nor taught in the aforesaid U.S. Pat. No. 3,973,179. More specifically, means are provided for selectively disabling the releasable latching means and precluding its inadvertent actuation once the mating sections are joined together. This means comprises a screw 42 carried by a threaded opening 43 in the hose section and accessible rearwardly thereof (below the switch as shown in FIGS. 2 and 7). This screw may be driven into the hose section (by means of a small screwdriver blade or other suitable implement, and within the spring) to bear against the rear portion of the latch 35 and preclude the latch from being manually recessed into the hose section, regardless of any subsequent attempted actuation of its integral release button 37. Thus, when the screw 42 is fully seated to disable and override the latch 35, an accidental jarring or attempted actuation of the release button 37 will have no consequential effect; and the hose section 12 will remain joined to the tool section 11, thereby precluding an inadvertent separation of the mating sections during operation of the tool. Conversely, to enable the latch to again become operative, the screw is withdrawn partially from its threaded recess (again by use of a suitable implement) to enable the latch to be withdrawn sufficiently within the hose section to allow the mating sections to become separated.

In addition, the tool section 11 is provided with a downwardly-projecting arcuate transverse ridge 44 formed integrally thereon, and the hose section 12 is provided with an externally-accessible arcuate transverse groove 45 formed thereon (as shown in FIGS. 2 and 5) to receive the ridge, when the sections are fully joined. The complementary interfitting ridge 44 and groove 45 provide good structural rigidity and preclude axial separation of the mating sections in a direction substantially parallel to the longitudinal axis of the tool.

Finally, with reference again to FIG. 1 and with further reference to FIG. 8, the power supply 18 comprises the usual transformer 46 and bridge rectifier 47 for supplying 12 volt D.C. power to the surgical cast cutter 10. The low-voltage cable 31 (carried by the flexible vacuum hose 16) is connected via cable 48 and plug 49 to a suitable receptacle 50 on the power supply 18. The end of the flexible hose, as at 51, is received within a suitable coupling 52 on the vacuum cleaner 17. The vacuum cleaner has a cable 53 terminating in a plug 54 received within a receptacle 55 on the power supply for supplying line voltage to the vacuum cleaner. The power supply has a cable 56 and plug 57 for plugging into the line 58. As shown in FIG. 8, a main switch 59 and fuse 60 are also provided.

Because of its modular "two section" construction, together with its low-voltage operation and vacuum exhaust to a remote vacuum cleaner, the improved surgical cast cutter of the present is also adaptable to a broad line of additional products for medical and other purposes, wherein similar operational and environmental characteristics may be encountered.

Obviously, many modifications may be made without departing from the basic spirit of the present invention. Accordingly, it will be appreciated by those skilled in the art that within the scope of the appended claims, the invention may be practiced other than has been specifically described herein.

I claim:

1. A surgical cast cutter, comprising a generally longitudinal tool section and a complementary hose section releasably secured to the tool section rearwardly thereof, first rib means formed transversely on the rearward portion of the tool section, second rib means formed transversely on the forward portion of the hose section and cooperating with the first rib means to slidably guide the sections into engagement with each other, the sections have respective housing edges inclined with respect to the first and second rib means, the housing edges substantially abutting one another when the sections are fully joined together, releasable latching means for retaining the sections together, electrical contact means carried by each of the sections and respectively engaging each other when the sections are joined together, the tool section having a housing with an electric motor therein, first conductor means connecting the motor to the respective contacts on the tool section, second conductor means connecting the respective contacts on the hose section to a source of power, an oscillating cutter mounted forwardly of the housing, a driving transmission means between the motor and the cutter, switch means for selectively energizing the motor, the housing having a debris conduit formed therein, the conduit commencing near the cutter and terminating in rearward opening in the tool section housing, the hose section having a forward opening formed therein and communicating with the rearward opening in the housing when the sections are joined together, means for substantially sealing the sections against air leakage therebetween adjacent to the communicating openings, and a vacuum hose carried by the hose portion, communicating with the opening therein, and extending rearwardly therefrom.

2. A surgical cast cutter, comprising a tool section and a complementary hose section releasably secured to the tool section, cooperating means for manually sliding the sections relative to one another, releasable latching means for retaining the sections together, means for selectively disabling the latching means to prevent the sections from being separated inadvertently, electrical contact means carried by each of the sections and respectively engaging each other when the sections are joined together, the tool section having a housing with an electric motor therein, conductor means for connecting the motor to the respective contacts on the tool section, an oscillating cutter mounted forwardly of the housing, a driving transmission means between the motor and the cutter, the housing having a debris conduit formed therein, the conduit commencing near the cutter and terminating in a rearward opening in the housing, the hose section having a forward opening formed therein and communicating with the rearward opening in the housing when the sections are joined together, means for substantially sealing the sections against air leakage therebetween adjacent to the communicating openings, a vacuum hose carried by the hose section and communicating with the opening therein, cable means carried by the vacuum hose and connected to the respective contacts on the hose section, and switch means carried by one of the sections for selectively energizing the motor.

3. A surgical cast cutter, comprising a tool section and a complementary hose section rearwardly of the tool section, cooperating means for manually sliding the sections relative to one another, releasable latching means for retaining the sections together, electrical contact means carried by each of the sections and respectively engaging each other when the sections are joined together, the tool section having a housing, a low-voltage electric motor in the housing, conductor means connecting the motor to the respective contacts on the tool section, an oscillating cutter mounted forwardly of the housing, a driving transmission means between the motor and the cutter, the housing having a debris conduit formed therein, the conduit commencing near the cutter and terminating in a rearward opening in the housing, the hose section having a forward opening formed therein and communicating with the rearward opening in the housing when the sections are joined together, means for substantially sealing the sections against air leakage therebetween adjacent to the communicating openings, a vacuum hose carried by the hose section and communicating with the opening therein, a low-voltage cable carried by the vacuum hose and connected to the respective contacts on the hose section, and switch means carried by one of the sections for selectively energizing the motor.

4. In a surgical cast cutter or other tool having a generally longitudinal axis, the combination of a pair of axially-disposed mating sections releasably joined together, a first pair of diametrically-opposed parallel ribs formed on the rearward portion of one of the sections in a direction substantially at right angles to the longitudinal axis thereof, a second pair of diametrically-opposed parallel ribs formed on the forward portion of the other mating section, the respective pairs of ribs being complementary to one another and slidably engaging each other as the mating sections are brought together in a direction substantially at right angles to the longitudinal axis, each of the sections having respective housing side edges formed on an incline with respect to the cooperating pairs of ribs, the one section having a first debris opening formed therein, the other section having a complementary second opening formed therein, the openings each being inclined with respect to the complementary pairs of ribs, whereby, as the complementary ribs slide relative to one another as the sections are brought together, the respective inclined side housing edges are brought into substantial abutting engagement with one another, and the inclined respective openings in the sections become alined with one another with substantially no air leakage between the sections and around the openings therein.

5. In a surgical cast cutter or other tool having a generally longitudinal axis, the combination of a pair of mating sections releasably joined together, a first rib means formed on the rearward portion of one of the sections in a direction substantially at right angles to the longitudinal axis thereof, a second rib means formed on the forward portion of the other mating section, the respective rib means being complementary to one another and slidably engaging each other as the mating sections are brought together in a direction substantially at right angles to the longitudinal axis, each of the sections having respective housing side edges formed on an incline with respect to the complementary rib means, the one section having a first debris opening formed therein, the other section having a complementary second opening formed therein, the openings each being inclined with respect to the complementary rib means, whereby, as the rib means slide relative to one another as the sections are brought together, the inclined respective side housing edges are brought into substantial abutting engagement with one another, and the inclined respective openings in the sections become alined with one another with substantially no air leakage between the sections and around the openings therein, and respective electrical contact means carried by each of the sections and engaging one another when the sections are fully joined together.

6. In a surgical cast cutter having a generally longitudinal axis, the combination of a pair of mating sections releasably joined together, a first rib means formed on the rearward portion of one of the sections, a second rib means formed on the forward portion of the other mating section, the respective rib means being complementary to one another and slidably engaging each other as the mating sections are brought together in a direction transverse to the longitudinal axis, each of the sections having respective housing side edges formed on an incline with respect to the cooperating rib means, whereby, as the rib means slide relative to one another as the sections are brought together, the inclined side housing edges are brought into substantial abutting engagement with one another, one of the sections having a downwardly-projecting transverse ridge formed therein, the other section having a transverse groove formed therein to receive the ridge when the sections are fully brought together, thereby preventing an axial separation of the sections, and releasable latching means for retaining the sections in their fully joined position.

7. In a surgical cast cutter or other tool having a generally longitudinal axis, the combination of a pair of mating sections releasably joined together, a first rib means formed on the rearward portion of one of the sections, a second rib means formed on the forward portion of the other mating section, the respective rib means slidably engaging each other as the mating sections are brought together in a direction substantially transverse to the longitudinal axis, each of the sections having respective housing side edges formed on an incline with respect to the cooperating rib means, whereby, as the rib means slide relatively to one another as the sections are brought together, the respective inclined side housing edges are brought into substantial abutting engagement with one another, manually-manipulatable releasable latching means for retaining the sections in their fully joined position, and means carried by one of the sections for disabling the releasable latching means and precluding inadvertent actuation thereof and consequent undesired separation of the sections, said last-named means being intended to be actuated by an implement.

8. A surgical cast cutter, comprising a tool section having generally longitudinal axis, a complementary hose section releasably secured to the tool section rearwardly thereof, a first rib means formed on the rearward portion of the tool section substantially at right angles to the longitudinal axis thereof, a second rib means formed on the forward portion of the hose section, the respective rib means being complementary to one another and slidably engaging each other as the sections are brought together in a direction substantially at right angles to the longitudinal axis of the tool section, the tool section having a housing with a low-voltage electric motor therein, an oscillating cutter mounted forwardly of the housing, a driving transmission means between the motor and the cutter, the housing having a debris conduit formed therein to one side of the motor and isolated therefrom, the conduit commencing near the cutter and terminating in a rearward opening in the housing, the hose section having a complementary forward opening formed therein, the openings being formed on an incline with respect to the complementary rib means, each of the sections having respective housing side edges formed on an incline with respect to the complementary rib means, whereby, as the rib means slide relative to one another in a direction substantially at right angles to the longitudinal axis of the tool section, the inclined respective side housing edges are brought into substantial abutting engagement with one another, and the inclined respective openings in the sections become alined with one another with substantially no air leakage between the sections and around the opening therein, manually-manipulatable releasable latching means for retaining the sections in their fully joined position, means carried by one of the sections for selectively disabling the latching means and preventing inadvertent actuation thereof, electrical contact means carried by each of the sections and respectively engaging each other when the sections are joined together, conductor means connecting the motor to the respective contacts on the tool section, a vacuum hose carried by the hose section and communicating with the opening therein, a low-voltage cable carried by the vacuum hose and connected to the respective contacts on the hose section, and switch means carried by one of the sections for selectively energizing the motor.

9. In a portable surgical cast cutter, the combination of separable housing sections slidably engaging one another, manually-releasable latching means for retaining the sections in a fully joined position, a low-voltage electric motor in one of the sections, the one section having a debris conduit formed therein and isolated from the motor, the other section having an opening formed therein and communicating with the debris conduit, a vacuum hose carried by the other section and communicating with the opening formed therein, a low-voltage cable means carried by the vacuum hose, first electrical contact means carried by the other section and connected to the cable means, and second electrical contact means carried by the one section and connected to the motor, the first and second contact means engaging each other when the sections are slidably joined together.

* * * * *